United States Patent
Greaves

(10) Patent No.: US 12,390,406 B2
(45) Date of Patent: Aug. 19, 2025

(54) PROCESS FOR TREATING KERATIN FIBERS USING A COMPOSITION COMPRISING A CARNITINE SALT OR CARNITINE DERIVATIVE SALT COMPRISING AN ALIPHATIC DICARBOXYLIC ACID ANION

(71) Applicant: L'OREAL, Paris (FR)

(72) Inventor: Andrew Greaves, Aulnay-Sous-Bois (FR)

(73) Assignee: L'OREAL, Paris (FR)

( * ) Notice: Subject to any disclaimer, the term of this patent is extended or adjusted under 35 U.S.C. 154(b) by 986 days.

(21) Appl. No.: 17/415,602

(22) PCT Filed: Dec. 19, 2019

(86) PCT No.: PCT/EP2019/086348
§ 371 (c)(1),
(2) Date: Jun. 17, 2021

(87) PCT Pub. No.: WO2020/127764
PCT Pub. Date: Jun. 25, 2020

(65) Prior Publication Data
US 2022/0062131 A1    Mar. 3, 2022

(30) Foreign Application Priority Data

Dec. 20, 2018    (FR) ..................... 1873554

(51) Int. Cl.
| | | |
|---|---|---|
| A61K 8/362 | (2006.01) | |
| A61K 8/41 | (2006.01) | |
| A61Q 5/00 | (2006.01) | |
| A61Q 5/12 | (2006.01) | |
| A61Q 7/00 | (2006.01) | |

(52) U.S. Cl.
CPC .............. *A61K 8/362* (2013.01); *A61K 8/416* (2013.01); *A61Q 5/00* (2013.01); *A61Q 5/12* (2013.01)

(58) Field of Classification Search
CPC .......... A61K 8/362; A61K 8/416; A61Q 5/00; A61Q 5/12; A61Q 7/00
See application file for complete search history.

(56) References Cited

U.S. PATENT DOCUMENTS

| 5,741,816 A | 4/1998 | Tsujihara et al. |
|---|---|---|
| 2008/0118458 A1* | 5/2008 | Giesen ................. A61K 8/9789 424/737 |
| 2013/0172414 A1 | 7/2013 | Wang et al. |
| 2018/0064619 A1 | 3/2018 | Brun et al. |

FOREIGN PATENT DOCUMENTS

| CN | 102512409 A | 6/2012 |
|---|---|---|
| DE | 19539859 A1 | 4/1997 |
| EP | 0978272 A1 | 2/2000 |
| EP | 1175898 A2 | 1/2002 |
| EP | 1800654 A2 | 6/2007 |
| EP | 2111852 A2 | 10/2009 |
| EP | 2165697 A1 | 3/2010 |
| FR | 2619007 A1 | 2/1989 |
| JP | H08-092180 A | 4/1996 |
| JP | 2003-526661 A | 9/2003 |
| JP | 2011-132191 A | 7/2011 |
| JP | 2011-132192 A | 7/2011 |
| KR | 10-2017-0014179 A | 2/2017 |
| WO | 98/30196 A1 | 7/1998 |
| WO | 02/074265 A1 | 9/2002 |
| WO | 2006/097205 A2 | 9/2006 |
| WO | 2007/003307 A1 | 1/2007 |
| WO | 2016/151139 A1 | 9/2016 |
| WO | 2018/218009 A2 | 11/2018 |
| WO | 2020/127767 A1 | 6/2020 |

OTHER PUBLICATIONS

JPH0892180A—Google English Translation (Year: 1996).*
Translation of Chinese Office Action for counterpart Application No. 201980082950.4, dated Nov. 2, 2022.
Translation of Chinese Office Action for counterpart Application No. 201980083854.1, dated Nov. 2, 2022.
Translation of Japanese Office Action for counterpart Application No. 2021-530964, dated Jun. 6, 2022.
Translation of Japanese Office Action for counterpart Application No. 2021-531402, dated Jul. 4, 2022.
International Search Report and Written Opinion for counterpart Application No. PCT/EP2019/086348, dated Apr. 6, 2020.
International Search Report and Written Opinion for counterpart Application No. PCT/EP2019/086353, dated Apr. 9, 2020.
Mcmichael, Amy J., "Hair Breakage in Normal and Weathered Hair: Focus on the Black Patient," Journal of Investigative Dermatology Symposium Proceedings, vol. 12, Issue 2, Dec. 2007, pp. 6-9.
Swift, J. Alan, et al., "Flexabrasion: A Method for Evaluating Hair Strength," Cosmetics and Toiletries Journal, vol. 116, Dec. 12, 2001, pp. 53-60.
Non-Final Office Action in U.S. Appl. No. 17/415,206, mailed Jul. 17, 2024, 11 pages.
Final Office Action in U.S. Appl. No. 17/415,206, mailed Dec. 30, 2024, 12 pages.
Advisory Action for copending U.S. Appl. No. 17/415,206, dated Apr. 14, 2025.

* cited by examiner

Primary Examiner — Kyung S Chang
(74) Attorney, Agent, or Firm — The Marbury Law Group, PLLC

(57) ABSTRACT

The present invention relates to a process for treating keratin fibers, comprising the application of a composition comprising at least one carnitine salt or carnitine derivative salt comprising an aliphatic dicarboxylic acid anion, for caring for and/or repairing keratin fibers.

7 Claims, No Drawings

PROCESS FOR TREATING KERATIN FIBERS USING A COMPOSITION COMPRISING A CARNITINE SALT OR CARNITINE DERIVATIVE SALT COMPRISING AN ALIPHATIC DICARBOXYLIC ACID ANION

CROSS REFERENCE TO RELATED APPLICATION

This is a national stage application of PCT/EP2019/086348, filed internationally on Dec. 19, 2019, which claims priority to French Application No. 1873554, filed on Dec. 20, 2018, both of which are incorporated by reference herein in their entireties.

TECHNICAL FIELD

The present invention relates to a process for treating keratin fibers, comprising the application of a composition comprising at least one carnitine salt or carnitine derivative salt comprising an aliphatic dicarboxylic acid anion, for caring for and/or repairing keratin fibers.

Context

The hair can be damaged and weakened by external atmospheric agents such as pollution and bad weather, and also by mechanical or chemical treatments, such as brushing, combing, dyeing, bleaching, permanent-waving, relaxing and repeated washing. The hair can be damaged and in the long term can become brittle.

Thus, in order to remedy this, it is usual to have recourse to hair compositions intended for conditioning the hair. However, the conditioning effect obtained via these hair treatments fades out rapidly over time, and does not have satisfactory persistence with respect to shampoo washes.

It is known that carnitine or a salt thereof, such as carnitine tartrate or carnitine lactate, can be used in hair compositions (see in particular DE 195 39 859, EP 1 800 654 and EP 2 111 852). However, these compositions are not always entirely satisfactory with regard to preventing the breakage of the hair, in particular during combing.

There is thus still a real need to develop a process for treating the hair which makes it possible to preserve or even improve the quality of the fiber in order to reduce the breakage thereof, in particular during combing and in a long-lasting manner, that is to say which exhibits satisfactory persistence with respect to shampoo washes.

The applicant has discovered, surprisingly, that all of these problems can be solved by the process according to the present invention involving the application to the hair of a composition comprising carnitine salts or carnitine derivative salts having one or more aliphatic dicarboxylic acid anions.

SUMMARY

According to a first aspect, a subject of the present invention is a process for treating keratin fibers, comprising:
i) a step of applying to the keratin fibers a composition (A) comprising at least one compound of formula (I):

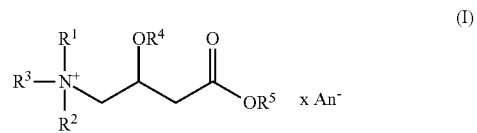

and the solvates thereof such as hydrates;
formula (I) wherein:
$R^1$, $R^2$ and $R^3$, which may be identical or different, represent a ($C_1$-$C_4$)alkyl group or ($C_1$-$C_4$) hydroxyalkyl group;
$R^4$ represents a hydrogen atom, a ($C_1$-$C_4$)alkyl group or a —C(O) R group, wherein R is a ($C_1$-$C_3$)alkyl group;
$R^5$ represents a hydrogen atom or a ($C_1$-$C_4$)alkyl group, an alkali metal or an alkaline-earth metal;
An⁻ represents an aliphatic dicarboxylic acid anion selected from the following compounds of formula (II):

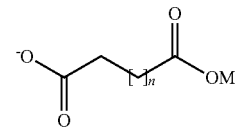

wherein:
n is an integer ranging from 2 to 8;
M represents a hydrogen atom, a negative charge, an alkali metal or an alkaline-earth metal;
x is a stoichiometric coefficient chosen so as to guarantee the electroneutrality of the compound of formula (I).

According to a second aspect, a subject of the present invention is a composition (A) as defined above.

According to a third aspect, a subject of the present invention is the cosmetic use of at least one compound of formula (I), as defined above, for caring for keratin fibers.

According to a final aspect, a subject of the present invention is the cosmetic use of at least one composition (A), as defined above, for caring for keratin fibers.

DETAILED DESCRIPTION

The term "keratin fibers" is intended to mean fibers of human or animal origin, such as the hair, body hair, the eyelashes, the eyebrows, wool, angora, cashmere or fur. According to the present invention, the keratin fibers are preferably human keratin fibers, more preferentially the hair.

The term "alkyl group" is intended to mean a linear or branched radical containing from 1 to 12 carbon atoms.

The term "($C_1$-$C_4$)alkyl group" is intended to mean an alkyl group comprising from 1 to 4 carbon atoms, preferably methyl, ethyl, n-propyl, isopropyl or butyl, more preferentially methyl or n-propyl, even more preferentially methyl.

The term "($C_1$-$C_3$)alkyl group" is intended to mean an alkyl group comprising from 1 to 3 carbon atoms, preferably methyl, ethyl, n-propyl or isopropyl, more preferentially methyl or n-propyl, even more preferentially methyl.

The term "($C_1$-$C_4$) hydroxyalkyl group" is intended to mean a ($C_1$-$C_4$)alkyl group, at least one of the hydrogen atoms of which is replaced with a hydroxyl (—OH) group.

The expression "at least one" is synonymous with the expression "one or more".

The expression "preventing the breakage of keratin fibers" is synonymous with the expression "increasing the mechanical strength of keratin fibers".

Treatment Process

According to a first aspect, a subject of the present invention is a process for treating keratin fibers as described above. Preferably, the treatment process may be a process for caring for and/or repairing keratin fibers.

The applicant has discovered, surprisingly, that the use of carnitine or of a derivative thereof in combination with a certain type of aliphatic dicarboxylic acid anions in the process according to the invention made it possible to improve the mechanical strength of keratin fibers and thus to reduce the breakage thereof, in particular during combing. Moreover, the applicant has also observed that it was possible to obtain a long-lasting effect over time with in particular a satisfactory persistence with respect to shampoo washes.

Composition (A)

According to a second aspect, a subject of the present invention is also a composition (A) as described above.

The composition (A) comprise at least one compound of formula (I) as defined above. The compound of formula (I) is a carnitine salt or a salt of a derivative thereof. The cationic portion of the compound of formula (I) is carnitine or a derivative thereof and the anionic portion $An^-$ of the compound of formula (I) is an aliphatic dicarboxylic acid anion.

Anionic Portion $An^-$ represents an aliphatic dicarboxylic acid anion selected from the following compounds of formula (II):

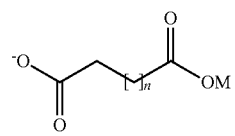

(II)

wherein:
n is an integer ranging from 2 to 8;
M represents a hydrogen atom, a negative charge, an alkali metal or an alkaline-earth metal.

Preferably, M represents a negative charge or a hydrogen atom.

Preferably, n is an integer ranging from 2 to 5.

In the case where M represents an alkali metal, it may be sodium.

The composition (A) may comprise a mixture of compounds of formula (I) comprising different aliphatic dicarboxylic acid anions $An^-$ selected from the compounds of formula (II) as defined above.

$An^-$ can preferably be selected from the following compounds of formula (IIa), (IIb), (IIc) or (IId):

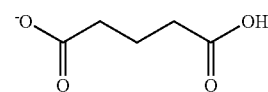

(IIa)

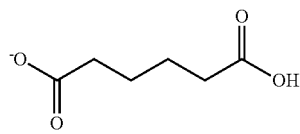

(IIb)

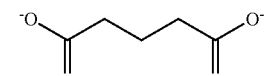

(IIc)

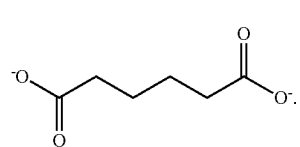

(IId)

The composition (A) may comprise a mixture of compounds of formula (I) comprising different aliphatic dicarboxylic acid anions $An^-$ selected from the compounds of formulae (IIa), (IIb), (IIc) or (IId) as defined above.

Preferably, $An^-$ can be selected from the compounds of formula (IIa), or (IIb) as defined above.

Cationic Portion

In the case where $R^5$ represents an alkali metal, it may be sodium.

The compound of formula (I) can preferably be a carnitine salt. Thus, $R^1$, $R^2$ and $R^3$ can preferably represent a methyl group and $R^4$ and $R^5$ can preferably represent a hydrogen atom.

The cationic portion of the compound of formula (I) can preferably be in the form of an optical isomer of L (levorotatory) or D (dextrorotatory) configuration, more preferentially of L configuration.

The compound of formula (I) can be selected from the following compounds of formulae (Ia), (Ib), (Ic) or (Id), and mixtures thereof:

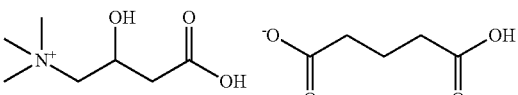

(Ia)

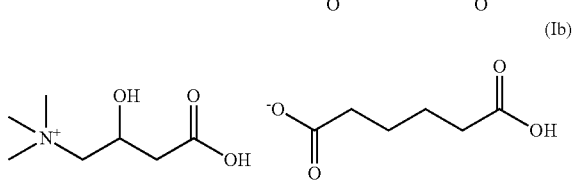

(Ib)

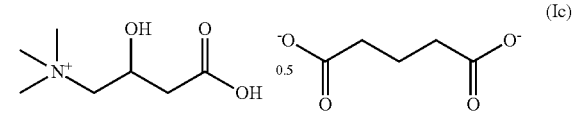

(Ic)

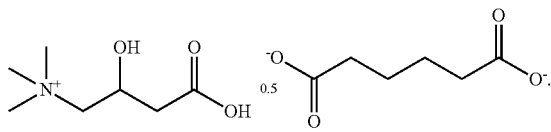

(Id)

The composition (A) can comprise a total content of compound(s) of formula (I) ranging from 0.1% to 100%, preferably from 0.5% to 50%, more preferentially from 0.5% to 20%, even more preferentially from 1% to 10% by weight relative to the total weight of the composition (A).

Other Elements/Ingredients

The composition (A) used in the process according to the present invention is a cosmetic composition, i.e. a composition which comprises a cosmetically acceptable medium, that is to say a medium compatible with human keratin fibers.

The composition (A) can comprise a solvent selected from the group constituted of water, $C_2$-$C_4$ alcohols, polyols, polyol ethers, and mixtures thereof. In this case, the compound of formula (I) can in particular be in dissociated form in the composition (A).

The composition (A) can comprise a solvent selected from the group constituted of water, ethanol, isopropanol, glycerol, propylene glycol, butylene glycol, pentylene glycol, hexylene glycol, dipropylene glycol, diethylene glycol, 2-butoxyethanol, propylene glycol monomethyl ether, diethylene glycol monoethyl ether, diethylene glycol monomethyl ether, and mixtures thereof.

Preferably, the composition (A) can comprise a solvent selected from the group constituted of water, ethanol, isopropanol, and mixtures thereof.

More preferentially, the composition (A) can comprise a solvent selected from the group constitutied of water, ethanol, and mixtures thereof.

The composition (A) can advantageously comprise a water/ethanol mixture comprising at least 10%, preferably at least 20%, more preferentially at least 30% by weight of ethanol. According to the latter embodiment, the composition (A) can in particular be formulated in the form of a lotion applied to dry keratin fibers, the use of ethanol making it possible to facilitate the wetting of the dry keratin fibers, the drying of the keratin fibers thus treated and also the diffusion of the active agents in the keratin fibers.

The composition (A) can also comprise at least one cosmetic ingredient selected from the group constituted of nonionic, anionic, cationic and amphoteric surfactants, vitamins and provitamins, including panthenol, fillers, colorants, nacreous agents, opacifiers, sequestrants, film-forming polymers, cationic, anionic or neutral polymers, associative polymers, plasticizers, silicones, thickeners, oils, antifoams, moisturizers, emollients, penetrants, fragrances, preserving agents, and mixtures thereof.

These usual cosmetic ingredients can be present in the composition (A) in usual amounts, which can be easily determined by those skilled in the art, and which can range, for each ingredient, from 0.01% to 20% by weight relative to the total weight of the composition (A). Those skilled in the art will take care to select the ingredients included in the composition (A), and also the amounts thereof, so that they are not detrimental to the properties of the composition.

The composition (A) can be in any galenical form conventionally used for a hair application. In a nonlimiting manner, the composition (A) can be in the form of a lotion, a cream, a mousse, a gel, a spray or a lacquer.

The composition (A) can be used by rinse-off or leave-on application.

The composition (A) can be in the form of a shampoo, a mask, a conditioning composition or a pre-shampoo. The composition (A) can also be in the form of a composition to be added to or mixed with, before application, a shampoo, a mask or a conditioning composition.

The composition (A) can be packaged in a pump dispenser bottle or in an aerosol container, in order to ensure application of the composition (A) in vaporized form (lacquer) or in mousse form. In these cases, the composition (A) preferably comprises at least one propellant.

pH of the Composition (A)

The composition (A) can have a pH ranging from 3 to 10, preferably from 4 to 7. The pH can be adjusted using an organic or mineral acid or an organic or mineral base normally used in the cosmetics industry.

Additional Characteristics Regarding the Process

The composition (A) may be applied to dry or wet keratin fibers, preferably to dry keratin fibers.

The bath ratio of the composition (A) applied to the keratin fibers can range from 0.1 to 10. The term "bath ratio" is intended to mean the ratio between the total weight of the applied composition (A) and the total weight of keratin fibers to be treated.

The process according to the present invention may comprise at least one additional step following on from step i) selected from the following steps ii) to iv):
  ii) a step of leaving the composition (A) on the keratin fibers, preferably for a period of at least 10 seconds;
  iii) a step of rinsing and/or washing the keratin fibers;
  iv) a step of drying the keratin fibers in ambient air or by means of a heating device.

Preferably, the process may comprise the additional steps ii) and iv) as described above and carried out in this order. More preferentially, the process may comprise all of the additional steps ii), iii) and iv) as described above and carried out in this order.

The leaving-on step can have a duration ranging from 10 seconds to 60 minutes, preferably from 30 seconds to 30 minutes.

The washing step may for example be carried out using a shampoo.

The temperature of the heating means may range from 45° C. to 230° C., preferably from 45° C. to 100° C., more preferentially from 50° C. to 80° C. A hairdryer, a heating hood, an iron or a heating brush may for example be used as heating means.

In the case where the process does not comprise step iii) of rinsing and/or washing the keratin fibers, the composition (A) may for example comprise a water/ethanol mixture which comprises at least 10%, preferably at least 20%, more preferentially at least 30% by weight of ethanol. The use of such a mixture makes it possible in particular to facilitate the evaporation of the composition.

Uses

According to a third aspect, a subject of the present invention is the cosmetic use of at least one compound (I), as described above, for caring for and/or repairing keratin fibers, preferably for preventing the breakage of keratin fibers. Any of the compounds (I) described above can be used for this purpose.

According to a final aspect, a subject of the present invention is the cosmetic use of a composition (A), as described above, for caring for and/or repairing keratin fibers, preferably for preventing the breakage of keratin fibers.

The examples that follow serve to illustrate the invention without, however, being limiting in nature.

EXAMPLES

In the text which follows, the term "alkaline solubility (AS)" is intended to mean the loss of mass of a sample of 100 mg of keratin fibers under the action of a decinormal sodium hydroxide solution for 30 min at 65° C.

Compounds Used in the Examples

The following compounds were used in the examples:

TABLE 1

| Compound | Name | Origin |
| --- | --- | --- |
| C1 | L-Carnitine adipate (Invention) | Synthesized |
| C2 | L-Carnitine glutarate (Invention) | Synthesized |
| C3 | L-Carnitine lactate (Comparative) | Synthesized |
| C4 | L-Carnitine tartrate (Comparative) | Synthesized |

TABLE 1-continued

| Compound | Name | Origin |
| --- | --- | --- |
| C5 | Adipic acid | Supplier: Aldrich Reference: A26357 |
| C6 | Glutaric acid | Supplier: Aldrich Reference: G3407 |
| C7 | DL-Lactic acid | Supplier: Aldrich Reference: 69785 |
| C8 | DL-Tartaric acid | Supplier: Aldrich Reference: T400 |

Synthesis of Compounds C1 to C4

The compounds C1 to C4 were synthesized according to the procedure described below.

Procedure 50 g of L-carnitine (M=161.19 g/mol; CAS: 541-15-1), i.e. 310 mmol, are weighed out into a single-necked flask and then 310 mmol of organic acid are added. 25 ml of ethanol are added. The mixture is stirred using a magnetic stirrer. The reaction mixture is heated in a water bath (bath temperature of 40° C.) for 30 min. It is left to cool with stirring. The solvent is evaporated under vacuum. Analyses are carried out in order to verify that the structures obtained are those expected.

Comparative Tests No. 1: Study of the "Prevention of Breakage Due to Repeated Combing" Effect Repeated Combing Test The test consists in vertically suspending a lock of hair then in combing the lock at a constant rate. The hairs lost during combing are collected and weighed. The greater the mass of hair lost, the more hair breakage there is.

Formulae Tested

The following formulae were prepared and then tested according to the procedure described below:

TABLE 2

| Formula No. | C1 | C2 | C3 | C4 | C5 | C6 | C7 | C8 | pH* | Water/ethanol-70/30 (v/v) |
| --- | --- | --- | --- | --- | --- | --- | --- | --- | --- | --- |
| 1 |  |  | 4g |  |  |  |  |  | 6 | q.s. for 100 g |
| 2 |  |  |  | 4g |  |  |  |  | 6 | q.s. for 100 g |
| 3 | 4 g |  |  |  |  |  |  |  | 6 | q.s. for 100 g |
| 4 |  | 4 g |  |  |  |  |  |  | 6 | q.s. for 100 g |
| 5 |  |  | 50 g |  |  |  |  |  | 6 | q.s. for 100 g |
| 6 |  |  |  | 50 g |  |  |  |  | 6 | q.s. for 100 g |
| 7 | 50 g |  |  |  |  |  |  |  | 6 | q.s. for 100 g |
| 8 |  |  |  |  | 50 g |  |  |  | 6 | q.s. for 100 g |
| 9 |  |  |  |  |  |  | 50 g |  | 6 | q.s. for 100 g |
| 10 |  |  |  |  |  |  |  | 50 g | 6 | q.s. for 100 g |
| 11 |  | 10 g |  |  |  |  |  |  | 4 | q.s. for 100 g |
| 12 |  |  |  |  |  | 10 g |  |  | 4 | q.s. for 100 g |
| 13 |  |  |  |  |  |  |  | 10 g | 6 | q.s. for 100 g |
| 14 |  |  |  |  |  |  |  |  | 6 | q.s. for 100 g |

*pH adjusted with NaOH/HCl

Procedure

The formulae are applied to locks of damaged hair (2.7 g/27 cm) as indicated in the table below. The locks are immediately wrapped in food wrap, then the locks are placed on a hot plate at the temperature indicated in the table below. They are left to stand for the time indicated in the table below. The food wrap is removed. The application is repeated if this is indicated in the table below. The locks are washed with DOP shampoo according to the washing protocol described below if this is indicated in the table below. They are dried under a hood (60° C., 10 min/g hair). The locks are then combed 30 times with a comb at a rate of 10 cm/s. The mass of hair lost during the combing is weighed.

Washing Protocol

The locks are wetted with tap water at 38° C. for 10 seconds, the shampoo (0.4 g/g of hair) is applied, the locks are massaged for 15 seconds and rinsed with water for 20 seconds.

TABLE 3

| Example | Formulation No. | g/g hair | Number of applications | Temp (° C.) | Application time (min) | Shampoo |
|---|---|---|---|---|---|---|
| 1 | 1 | 0.5 | 3 | 27 | 5 | No |
| 2 | 2 | 0.5 | 3 | 27 | 5 | No |
| 3 | 3 | 0.5 | 3 | 27 | 5 | No |
| 4 | 4 | 0.5 | 3 | 27 | 5 | No |
| 5 | 1 | 10 | 1 | 45 | 40 | Yes |
| 6 | 2 | 10 | 1 | 45 | 40 | Yes |
| 7 | 3 | 10 | 1 | 45 | 40 | Yes |
| 8 | 5 | 10 | 1 | 45 | 40 | Yes |
| 9 | 6 | 10 | 1 | 45 | 40 | Yes |
| 10 | 7 | 10 | 1 | 45 | 40 | Yes |
| 11 | 8 | 10 | 1 | 45 | 40 | Yes |
| 12 | 9 | 10 | 1 | 45 | 40 | Yes |
| 13 | 10 | 10 | 1 | 45 | 40 | Yes |
| 14 | 11 | 2 | 3 | 27 | 5 | No |
| 15 | 12 | 2 | 3 | 27 | 5 | No |
| 16 | 13 | 0.5 | 5 | 27 | 5 | No |
| 17 | 14 | 5 | 1 | 27 | 10 | No |
| 18 | 14 | 10 | 1 | 45 | 40 | Yes |

Results

TABLE 4

| Example | Invention/Comparative | Hair loss (g) |
|---|---|---|
| 1 | Comparative | 0.354 |
| 2 | Comparative | 0.389 |
| 3 | Invention | 0.172 |
| 4 | Invention | 0.132 |
| 5 | Comparative | 0.384 |
| 6 | Comparative | 0.359 |
| 7 | Invention | 0.249 |
| 8 | Comparative | 0.268 |
| 9 | Comparative | 0.229 |
| 10 | Invention | 0.141 |
| 11 | Comparative | 0.227 |
| 12 | Comparative | 0.182 |
| 13 | Comparative | 0.232 |
| 14 | Invention | 0.093 |
| 15 | Comparative | 0.296 |
| 16 | Comparative | 0.317 |
| 17 | Comparative | 0.383 |
| 18 | Comparative | 0.246 |

Conclusions for Examples 1 to 4

The results obtained for examples 1 to 4 show that there is less hair breakage when the locks are treated with a composition comprising L-carnitine adipate (invention) or L-carnitine glutarate (invention) than when the locks are treated with a composition comprising L-carnitine lactate or L-carnitine tartrate.

Conclusions for Examples 5 to 7

The results obtained for examples 5 to 7 show that there is less hair breakage when the locks are treated with a composition comprising L-carnitine adipate (invention) than when the locks are treated with a composition comprising L-carnitine lactate or L-carnitine tartrate under application conditions different from examples 1 to 4.

Conclusions for Examples 8 to 13

The results obtained for examples 8 to 13 show that there is less breakage when the locks are treated with a composition comprising a high concentration (50% by weight) of L-carnitine adipate (invention) than when the locks are treated with a composition comprising a high concentration (50% by weight) of L-carnitine lactate or L-carnitine tartrate or adipic acid or lactic acid or tartaric acid.

Conclusions for Examples 14 and 15

The results obtained for examples 14 and 15 show that there is less breakage when the locks are treated with a composition at pH 4 comprising L-carnitine glutarate than when the locks are treated with a composition at pH 4 comprising glutaric acid.

Comparative Tests No. 2: Study of the "Persistence with Respect to Shampoo Washes of the Prevention of Breakage" Effect by Means of the Flexabrasion Test Formulae Tested The following formulae were prepared and then tested according to the procedure described below:

TABLE 5

| | Ingredients | |
|---|---|---|
| Formula No. | L-Carnitine glutarate | Water/ethanol - 70/30 (v/v) |
| 15 | 3 g | q.s. for 100 g |
| 16 | 10 g | q.s. for 100 g |
| 17 | — | q.s. for 100 g |

TABLE 6

| Example | Formula No. |
|---|---|
| 19 | 15 |
| 20 | 16 |
| 21 | 16 |
| 22 | 17 |

Procedure (Examples 19, 20 and 22)

0.4 g of formula (formulae 15 to 17) to be tested/g hair is applied to locks of damaged hair (2.7 g/27 cm; alkaline solubility of 40). The locks are immediately wrapped in food wrap, then the locks are placed on a hot plate maintained at a temperature of 33° C. They are left to stand for 5 minutes. The food wrap is removed. The locks are washed with DOP shampoo according to the washing protocol described below. They are dried under a hood (60° C., 10 min/g hair). The cycle of applying the formula, washing and drying is repeated four times so as to have a total of 5 applications of the formula to be tested.

Procedure (Example 21)

0.4 g of formula 16 to be tested/g hair is applied to locks of damaged hair (2.7 g/27 cm; alkaline solubility of 40). The locks are immediately wrapped in food wrap, then the locks are placed on a hot plate maintained at a temperature of 33° C. They are left to stand for 5 minutes. The food wrap is removed. The application is repeated four times so as to have a total of 5 applications of the formula to be tested. The locks are washed with DOP shampoo according to the washing protocol described below. They are dried under a hood (60° C., 10 min/g hair). The shampooing and drying cycle is repeated four times so as to have a total of 5 shampooing and drying cycles.

Washing Protocol

The locks are wetted with tap water at 38° C. for 10 seconds, the shampoo (0.4 g/g of hair) is applied, the locks are massaged for 15 seconds and rinsed carefully with water for 20 seconds.

The locks of examples 19 to 22 were tested according to the Flexabrasion test described below.

Flexabrasion Test

The Flexabrasion technique is known to those skilled in the art for the breakage of keratin fibers (references: Flexabrasion: A Method for Evaluating Hair Strength, Cosmetics & Toiletries Journal, Jun. 26, 2009 and Hair Breakage in Normal and Weathered Hair: Focus on the Black Patient, Journal of Investigative Dermatology Symposium Proceedings, Volume 12, Issue 2, December 2007, Pages 6-9). The principle of the test is to measure the time taken for hair fibers subjected to a mechanical stress to break (flexure and abrasion). A Flexabrasion device (Fiberstress model from the company Textechno) is used. A strand of hair is attached to a 20 g weight at one end and the other end is attached to an immobile bar. The strand of hair moves back and forth on a 300 µm stainless steel wire. The movement has an amplitude of 10 mm and a frequency of 0.5 Hz. The breakage is detected by an optical sensor which measures the breakage time (in seconds). A series of measurements comprises 75 strands of hair.

Results

TABLE 7

| Example | Median drop time (s) |
|---|---|
| 19 | 1114 |
| 20 | 1296 |
| 21 | 1240 |
| 22 | 662 |

The results show that, even after 5 shampoo washes, there is still a better performance quality in terms of prevention of hair breakage compared with the placebo (example 22). Thus, the treatment process according to the present invention is particularly resistant to shampoo washes.

The invention claimed is:

1. A method for washing or conditioning hair with a composition (A), comprising a step of:
   (i) applying to the hair the composition (A) comprising at least one compound selected from formulae (Ia), (Ib), (Ic), (Id) and mixtures thereof:

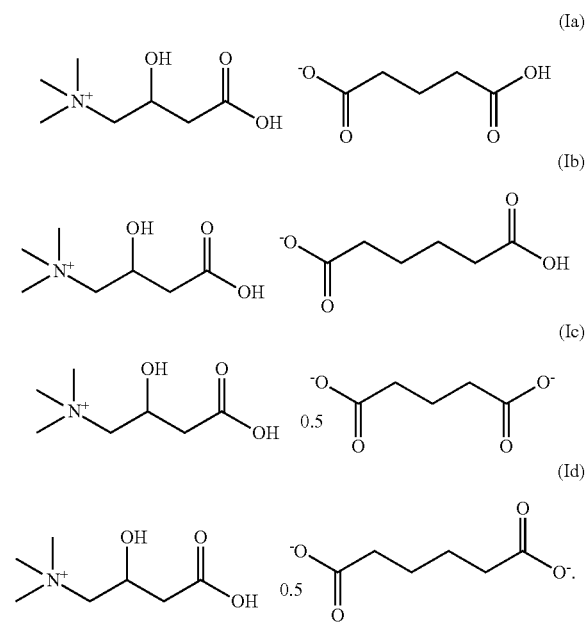

2. The method of claim 1, wherein cationic portion of the at least one compound selected from formulae (Ia), (Ib), (Ic), (Id) and mixtures thereof is in the form of an optical isomer of L or D configuration.

3. The method of claim 1, wherein the total amount of the at least one compound selected from formulae (Ia), (Ib), (Ic), (Id) and mixtures thereof ranges from 0.5% to 50%, by weight relative to the total weight of the composition (A).

4. The method of claim 1, wherein the composition (A) further comprises a solvent selected from water, $C_2$-$C_4$ alcohols, polyols, polyol ethers, and mixtures thereof.

5. The method of claim 1, wherein the composition (A) further comprises a solvent comprising water and ethanol, wherein the solvent comprises at least 10% ethanol by weight, relative to the total weight of the solvent.

6. The method of claim 1, wherein the composition (A) is applied to dry hair.

7. The method of claim 1, further comprising at least one of steps (ii), (iii), and/or (iv) after step (i), wherein if two or more of steps (ii), (iii), and/or (iv) are performed, the two or more steps are performed in any order after step (i):
  ii) leaving the composition (A) on the hair for a period of at least 10 seconds;
  iii) rinsing and/or washing the hair; or
  iv) drying the hair.

\* \* \* \* \*